United States Patent
Chang et al.

(10) Patent No.: US 7,405,181 B2
(45) Date of Patent: Jul. 29, 2008

(54) BIO-FERTILIZER COMPOSITION FOR PROMOTING GROWTH OR ORCHID PLANTS AND APPLICATION

(75) Inventors: Doris Chi-ning Chang, Taipei (TW); Ling-chin Chou, Taipei (TW); Ming-chi Lee, Taipei (TW)

(73) Assignee: National Taiwan University, Taipei (TW)

(*) Notice: Subject to any disclaimer, the term of this patent is extended or adjusted under 35 U.S.C. 154(b) by 555 days.

(21) Appl. No.: 11/033,715

(22) Filed: Jan. 13, 2005

(65) Prior Publication Data
US 2006/0154821 A1    Jul. 13, 2006

(51) Int. Cl.
| | |
|---|---|
| A01N 63/00 | (2006.01) |
| C05F 11/02 | (2006.01) |
| A01H 17/00 | (2006.01) |
| A01P 21/00 | (2006.01) |
| A01D 9/02 | (2006.01) |
| C05D 9/02 | (2006.01) |
| A01H 7/00 | (2006.01) |
| A01P 13/00 | (2006.01) |

(52) U.S. Cl. .............. 504/117; 71/11; 71/24; Plt./311

(58) Field of Classification Search .......... 71/24, 71/11; 504/116, 117
See application file for complete search history.

(56) References Cited

U.S. PATENT DOCUMENTS
4,799,950 A * 1/1989 Suzuki et al. ............... 504/140

FOREIGN PATENT DOCUMENTS
| AU | 8139475 | * 11/1976 |
| WO | WO0107380 A | * 2/2001 |

OTHER PUBLICATIONS

X.C. Shan, Characterization and Taxonomic Placement of Rhizoctonia-like Endophytes from Orchid Roots, 2002, Mycologia, vol. 94, Issue 2, pp. 230-239.*
Chun-Ching Lin, Antioxidant and Hepatoprotective Effects of *Anoectochilus formosanus* and *Gynostemma pentaphyllum*, American Journal of Chinese Medicine, 2000, Winter, pp. 1-9.*

* cited by examiner

Primary Examiner—Johann R. Richter
Assistant Examiner—Andriae M Holt
(74) Attorney, Agent, or Firm—Bacon & Thomas PLLC

(57) ABSTRACT

Disclosed is a bio-fertilizer composition for promoting growth of orchid plants. The composition comprises a symbiotic organism, a growth substance; and a medium, which is used to mix and evenly disperse the symbiotic organisms and the growth substance. The symbiotic organism is selected from the group consisting of *Rhizoctonia* sp. (BCRC930076) and *Rhizoctonia* sp. (BCRC930077). The bio-fertilizer composition according to the invention can promote the growth of orchid plants, increase the flowering rate and flowering quality, decrease the occurrence of root disease to prevent the usage of pesticide, and increase the beneficial components toward human health of medicinal orchids.

10 Claims, 3 Drawing Sheets

BIO-FERTILIZER COMPOSITION FOR PROMOTING GROWTH OR ORCHID PLANTS AND APPLICATION

BACKGROUND OF THE INVENTION

1. Field of the Invention

The present invention relates to a bio-fertilizer composition, especially relates to a composition containing symbiotic organisms for promoting growth of orchid plants.

2. The Prior Arts

Proper fertilizers are important to crops during growth stages since the nutrients in soil may not fully meet the needs. Fertilizer for crops may be classified as chemical fertilizer, bio-fertilizer, green manure and compost. Bio-fertilizer contains microbes or enzymes, and is available in the forms of powder, granule or liquid. When bio-fertilizers are applied on the seeds, seedlings or soils, not only the effectiveness of nutrient uptake can be improved, but also the amount of beneficial microbes can be replenished to maintain soil in good eco-environment. The nutrient level in soil is further elevated, with soil fertility enhanced, nutrient uptake assisted, and the abilities of disease-resistant, drought-enduring, and cold-resistant of crops enhanced. In general, the advantages may be grouped into 3 categories: (1) nitrogen fixation, to fix atmospheric nitrogen into ammonia, and convert into nitrate which can be used by crops, (2) solubilization of soil minerals such as phosphorus, calcium and iron to be used by plants, (3) promotion of the nutrient uptake by roots and plant growth.

The Orchid family, *Orchidaceae*, is one of the most numerous and biggest vascular bundle family. There are more than 80 genuses being identified so far, which stand for more than 20,000 species worldwide. They can be traced from gloomy fresh tropical rainforests to steep cliffs to dry desert regions. Many orchids have medicinal properties besides ornamental importance, such as *Dendrobium* and *Anoectochilus* which are of great commercial values. Many of the orchid strains have the problems of low germination rates and low asexual reproduction (agamogenesis) rates. The price of orchids is therefore very high with the long planting and cultivation time.

Orchid plants have difficulties in cultivation, slow growth, perplexity in flowering promotion, and numerous problems regarding transplanting, manure, watering, light management and so on. Orchids are mainly propagated using tissue culture techniques, but the survival ability and growth of the seedling are very slow after being transplanted from the cultivating vessels. Many chemical fertilizers in the market containing fixed ratio of inorganic substances, a formula for in common use, are for general purpose but not aimed at certain plants. Therefore, no specific effect is observed. On the other hand, the studies in soil have demonstrated that inorganics have complicated interactions with each other. Increasing the amount of one inorganic will affect the uptake rate of other inorganics, and result in lack of other inorganics. And for the application of organic fertilizers, the main problem is to emphasize the effective use of animal droppings but not to determine the requirement terms of orchids on each element. Animal droppings usually contain low nutrient levels, but organic fertilizers retain moisture contents and nutrients, also release in a slower rate. Though organic fertilizers increase plant growth in the beginning for orchids planting, result in rotten roots of plants after a period of time. This is because of the decomposing of animal droppings, which makes water and air blocked, an ideal environment for bacteria growth. Therefore, the growth rates and yields of orchid plants are decreased. In addition, pathogens and weed may hide in animal droppings to destroy plants.

In summary, applying fertilizer is necessary during orchid planting stage, but the objective is incapable of fulfillment with the lacks and disadvantages of chemical fertilizers and organic fertilizers in the market.

SUMMARY OF THE INVENTION

A primary object of the present invention is to provide a bio-fertilizer composition to solve the problems of above-mentioned techniques and promote growth of orchid plants.

To fulfill the objective of the present invention, the bio-fertilizer composition according to the invention comprises:

a symbiotic organism, which is selected from the group consisting of *Rhizoctonia* sp. (BCRC930076) and *Rhizoctonia* sp. (BCRC930077);

a growth substance; and a medium, which is used to mix and evenly disperse the symbiotic organisms and the growth substance.

The bio-fertilizer composition can be applied to promote orchid seed germination in test tubes, or be applied in seedling growth after deflasking to reach the goals of promoting planting, preventing disease, and increasing the beneficial components toward human health of medicinal orchids. In addition, the composition also increases the flowing rate and flowing quality. The bio-fertilizer composition can be used in a way to increase the yield of orchid seedlings and flowering plants to decrease the impact of chemical fertilizers toward environment.

The invention provides a bio-fertilizer composition containing symbiotic organisms for orchid growth, and can be applied in planting orchids to increase the propagation efficiency of seedling, also to breed disease-resistant, easy planting, high yield and more beautiful orchid strains.

The present invention is further explained in the following embodiment illustration and examples.

The present invention disclosed above is not limited by these examples. The present invention may be altered or modified by people skilled in the art and all such variations are within the scope and spirit of the present invention.

DETAILED DESCRIPTION OF THE PREFERRED EMBODIMENT

Figure 1:
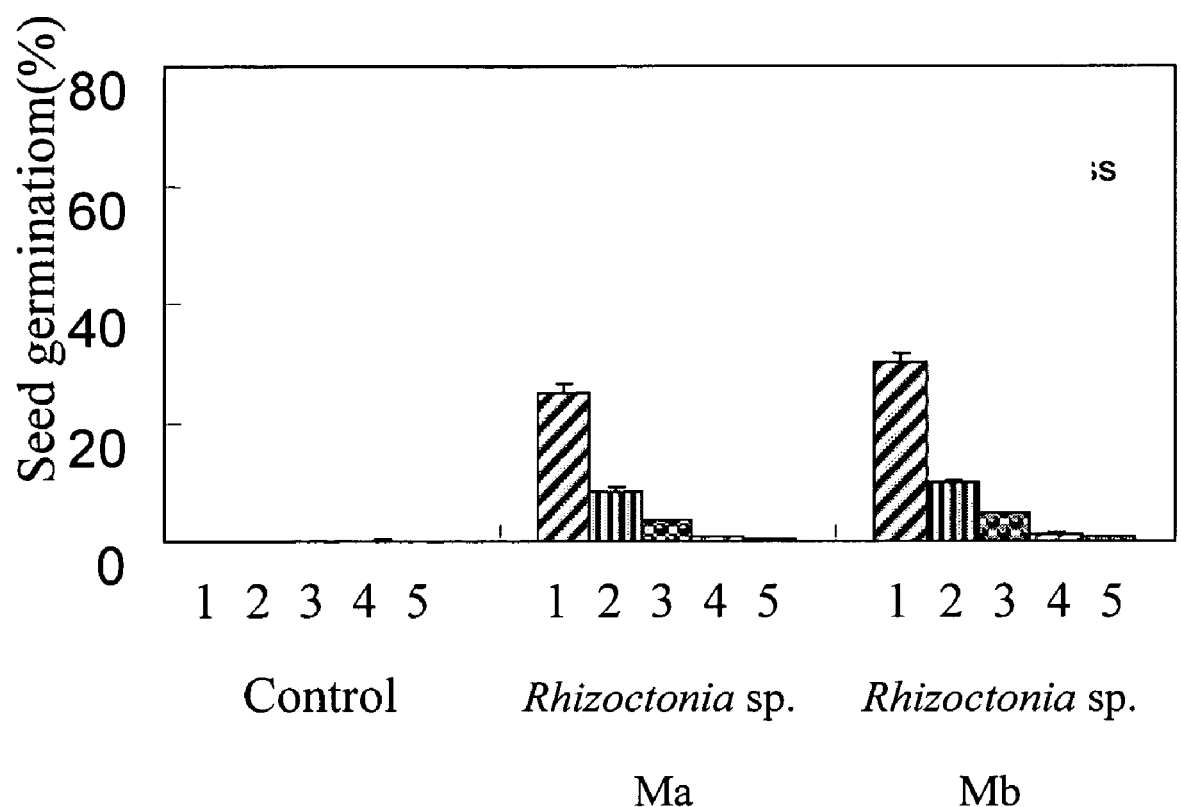
FIG. 1 shows the effects of bio-fertilizer compositions in the invention to *Haemaria* seeds germination rates. Number 1 to 5 indicates different culture media. 1. PDA culture media; 2. peat; 3. vermiculite; 4. perlite; and 5. Sphagnum mosses.

The bio-fertilizer composition of the present invention comprises a symbiotic organism, which is selected from the group consisting of *Rhizoctonia* sp. (BCRC930076) and *Rhizoctonia* sp. (BCRC930077); a growth substance; and a medium, which is used to mix and evenly disperse the symbiotic organisms and the growth substance. The symbiotic organisms are *Rhizoctonia* spp. purified and isolated from the wild grown orchid roots. One colony of *Rhizoctonia* sp., which has been deposited in FIRDI (Food Industry Research and Development Institute Taiwan, 331 Shih-Pin Road, Hsin-chu, Taiwan 300) with a deposit number of BCRC0930076, are pale yellow with cotton fibers in the front sides, and the colors of hyphae are also pale yellow. The widths of hyphae are between 3.5-4.5 mm, in average of 3.9 mm. The lengths of bead-like cells are between 17-30 mm, in average of 23.5 mm, and the widths are between 10-12 mm, in average of 11.1 mm. The rate of hyphal elongation is 10-11 mm per day. There are two nuclei in one cell. Another colony of *Rhizoctonia* sp., which has been deposited in FIRDI with a deposit number of BCRC0930077, are white yellow with cotton fibers in the front sides, and the colors of hyphae are also white yellow. The widths of hyphae are between 4-5 mm, in average of 4.34 mm. The lengths of bead-like cells are between 14-25 mm, in average of 19.4 mm, and the widths are between 9.6-14 mm, in average of 11.9 mm. The rate of hyphal elongation is 10-11 mm per day. There are two nuclei in one cell. The above-identified colonies were deposited on Dec. 15, 2004.

Any known plant growth substance (PGS) which promotes orchid growth and does not interfere with the existence of orchid symbiotic organism can be applied in the present invention and is not limited. The plant growth substances include natural plant hormones and artificially synthesized plant growth regulators. The natural plant hormones include auxins, gibberellins, cytokines, abscisic acid, ethylene, brassinosteroids, jasmonate and salicylates and so on, not restricted to the list here. The plant growth regulators are synthesized by chemical methods which are organics similar to the molecular structures or physiological activities of natural plant hormones. Examples are choline chloride, inositol, Lysine#3 root inducer and Aminosong solution, and are not limited to this list.

On the other hand, as a medium mentioned above, any medium used to thoroughly mix and evenly disperse the symbiotic organisms and the growth substances can be applied in the present invention to bring into functions, no particular restriction is applied in the invention. Examples include peat moss, Sphagnum mosses, coconut fiber and rotting logs, and are not limited to the list here.

The mixing ratio of symbiotic organisms and plant growth substances of the bio-fertilizer composition in the invention can be adjusted according to the spreading ways, amount, and different growth stages of orchid species. There is no particular restriction.

People skilled in the art of the present invention also understand from this explanation that the bio-fertilizer composition can be produced in either solid forms or in liquid forms.

On the other hand, people skilled in the art also comprehend that the symbiotic organism of the bio-fertilizer composition can be applied directly into the culture media of orchid seed in test tubes during seed germination without plant growth substance but with simple medium (e.g. oat meal agar medium) to promote the germination.

Besides, the bio-fertilizer composition can further comprises a nutrient solution to provide a better growth promotion effect. Any nutrient solution provides nutrients for orchid plants and enhances the growth can be applied in the present invention without particular restriction. Fruit and vegetable juices (for instance, V8 juice), GY nutrient solution (liquid glucose-yeast extract media), CM nutrient solution (glucose-yeast extract-malt extract) and food grade beverage (for instance, milk) are examples but not limited.

The present invention is further explained in the following examples. The present invention disclosed above is not limited by these examples. The present invention may be altered or modified and all such variations are within the scope and spirit of the present invention.

EXAMPLE 1

Isolation and Purification of Orchid Symbiotic Organisms

Orchids are observed after slicing of each orchid plant under microscope, and the roots suspected to be infected with orchid symbiotic organisms are sampled to isolate the microbes from the infected roots. First of all, the roots are washed, sonicated with 1% sodium hypochlorite for 15 to 20 min for disinfection, then washed with sterile distilled water three times. The roots are cut into pieces, placed in separation culture media, and incubated in the dark at 25° C. for 3 to 4 days till mycelia appear. Single hypha picked from mycelium is subcultured into potato dextrose agar (PDA) plate (39 g/L of DIFCO potato dextrose agar) for colony purification. Purification of hypha is determined according to the growth condition of hypha, and the non-purified hypha is picked with a needle, incubated in a fresh PDA plate till colonies are purified. Purified colonies are placed into test tubes respectively and stored at 4° C.

The purified symbiotic organisms are identified, termed *Rhizoctonia* sp. Ma and *Rhizoctonia* sp. Mb by FIRDI (Taiwan, ROC), and deposited there on Dec. 15, 2004. The deposit number is assigned to be BCRC930076 and BCRC930077, respectively.

EXAMPLE 2

Analysis on the Pathogenicity of Orchid Symbiotic Organisms

Both *Rhizoctonia* sp. Ma and *Rhizoctonia* sp. Mb are analyzed for their pathogenicities to affirm their danger to plants.

Sterilized peat mosses or soil-free media are used as the growing media for testing plants. First of all, the surfaces of seeds are disinfected with sodium hypochlorite, these seeds includ crop blocks such as mung beans (bean family), cucumbers (calabash family), radishes (crucifer family) or rice and so on. These disinfected seeds are sowed directly, or germinated in advance, and placed into the media containing purified orchids symbiotic organisms, in the ratio of 0.5-1 g microbes to one plant in a plastic vessel respectively. The water level is adjusted to be the same as in the field. The container and the plant are wrapped with a large transparent plastic bag to prevent the spreading of harmful microbes, and the plant was kept away from the side of bag to avoid the abnormal growth. These bags are placed in a green house with normal illumination for 7-14 days. The growth of each plant is observed to confirm whether it has symptoms. Finally, no symptom is observed. Therefore these symbiotic organisms obtained in this experiment show no pathogenicity.

EXAMPLE 3

Preparation of the Bio-Fertilizer Composition

Culture media containing 39 g of Difco PDA (potato dextrose agar) in one liter of water are autoclaved at 121° C. for 20 minutes to cultivate the purified orchid symbiotic organisms obtained from Example 1, which are stored as the seed stocks.

The orchid symbiotic organisms can be cultivated and produced in liquid form or solid form. GY culture solution (2% of glucose and 1% of yeast extract), CM culture solution (5 g each of glucose, yeast extract and malt extract are added to one liter media), and MP culture media (2.5% of milk powder) are applied for liquid form cultivation. These culture solutions are autoclaved for 20 min to be sterile. After the media are cooled, the abovementioned orchid symbiotic microbial seed stocks are inoculated to cultivate either stay quiet at 25° C. or shake at low speed (80-100 rpm). Five days later, the solution of culture media ias ground with a disinfected juice grinder to disperse the mycelium and stored in a sprinkling can.

When orchid symbiotic organisms is cultivated in solid form, media for cultivation of mushroom or mushroom spawn or orchid such as peat moss, Sphagnum mosses, coconut fiber or rotting logs are mixed thoroughly in a ratio with the abovementioned liquid culture solution and autoclaved for 60 min. After the media are cooled, the abovementioned orchid symbiotic microbial seed stocks are inoculated in the surface of this medium. Cultivation can be carried out in the dark in sterile compact packs or in shallow dishes less than 1.5 cm thick). After several days, when the mycelium grows all over the surface of media, the mycelium can be mixed evenly and used for inoculation, or be dried with media in the shade in a sterile environment, then put into sealing bags and store at 4° C. refrigerator, the mycelium can be stored for more than 6 months.

The proper cultivating temperature for orchid symbiotic organisms is around 25-28° C., usually without illumination. The bio-fertilizer composition of the invention is prepared after the orchid symbiotic organisms are mixed with plant growth substances and suitable media.

EXAMPLE 4

Enhancement of *Haemaria* Seed Germination

*Rhizoctonza* sp. Ma and *Rhizoctonia* sp. Mb isolated from Example 1 are spread into different culture media, such as PDA culture media, peat, vermiculite, perlite and Sphagnum mosses. The seeds of *Haemaria* are inoculated into the abovemetioned culture media to observe the germination.

FIG. 1 shows the results of germination rates with different treatments. *Haemaria* seeds do not germinate no matter what kind of culture media is used without the addition of orchid symbiotic mibrobe (Control group). And germination rates are significant higher than those of control groups when the orchid symbiotic organisms are added. Among them, the germination rate of the PDA culture media group is the highest, which reached 25-30%.

EXAMPLE 5

Enhancement of *Haemaria* Seedling Growth with Different Fertilizers During Tissue Culture The seedlings of *Haemaria* (about 1 cm in height) are planted in oat culture media (2.5 g of ground oat bran and 11.5 g of agar, add water to one liter) and divided into four groups; no fertilizer group (NM, control group); Hyponex No. 3 (commercial chemical fertilizer) added group; bio-fertilizer composition Ma added group (Ma) as described in Example 3 containing *Rhizoctonia* sp. Ma (BCRC930076); and bio-fertilizer composition Mb added group (Mb) as described in Example 3 containing *Rhizoctonia* sp. Mb (BCRC930077). The growth of seedlings of *Haemaria* in different groups is compared after 4 months. Each treatment contains 15 duplicates, and the data is analyzed with Duncan's multiple range test (DMRT) using p-value of 0.05.

As shown in Table 1, the addition of fertilizers significantly enhances the growth conditions of plants in comparison with the plants of the control group. Among the three former groups, Hyponex No. 3 added group shows the significantly enhancing effects in plant heights only, while the bio-fertilizer composition added groups show significant effects in plant heights, leave lengths and fresh weights when compared to the control group. Other values such as leave widths and root numbers are also higher than those of the control group though not significantly. In summary, the bio-fertilizer composition in the present invention indeed effectively improves the growth of the seedlings of *Haemaria*, and is better than the effects of chemical fertilizer.

TABLE 1

Growth of *Haemaria* seedling during tissue culture after 4 months of fertilizer addition

| Treatment | Plant height (cm) | Leave number | Leave length (cm) | Leave width (cm) | Root number | Fresh weight (g) |
|---|---|---|---|---|---|---|
| NM | 5.1$^b$ | 1.9$^a$ | 1.2$^b$ | 0.7$^a$ | 3.6$^a$ | 278.7$^b$ |
| Hyponex No. 3 | 5.3$^a$ | 2.0$^a$ | 1.2$^b$ | 0.7$^a$ | 3.7$^a$ | 390.8$^b$ |
| Ma | 5.8$^a$ | 2.0$^a$ | 1.7$^a$ | 0.9$^a$ | 4.4$^a$ | 538.3$^a$ |
| Mb | 5.9$^a$ | 2.2$^a$ | 1.7$^a$ | 0.9$^a$ | 5.0$^a$ | 567.6$^a$ |

EXAMPLE 6

Enhancement of *Haemaria* Seedling Growth in Different Heights During Tissue Culture The seedlings of *Haemaria* (6-9 cm in height) are divided into 2 groups by heights (6-7 cm in height vs 8-9 cm in height) and planted in oat culture media. Each group is further divided into 3 groups: no fertilizer group (NM control group); bio-fertilizer composition Ma (BCRC930076) added group from Example 3; and bio-fertilizer composition Mb (BCRC930077) added group from Example 3. The growth of seedlings of *Haemaria* in different groups is compared after 4 months. Each treatment contains 20 duplicates, and the data is analyzed with Duncan's multiple range test (DMRT) using p-value of 0.05.

As shown in Table 2, the addition of fertilizers (treatment groups) shows significant effects on both of the seedlings of *Haemaria* in plant heights, leave numbers and fresh weights in comparison with those of the plants from the control group, and showed better growth conditions.

TABLE 2

Growth of *Haemaria* seedling in different sizes during tissue culture after 4 months of bio-fertilizer addition

| Seedling size | Treatment | Plant height (cm) | Leave number | Leave length (cm) | Leave width (cm) | Root number | Node number | Fresh weight (g) |
|---|---|---|---|---|---|---|---|---|
| 6-7 cm | NM | $10.1^c$ | $3.8^b$ | $2.6^b$ | $1.5^b$ | $2.6^d$ | $5.6^b$ | $2.6^c$ |
|  | Ma | $10.7^c$ | $4.4^{ab}$ | $3.2^{ab}$ | $1.9^a$ | $3.0^c$ | $6.8^a$ | $3.7^b$ |
|  | Mb | $10.6^c$ | $4.0^b$ | $3.6^{ab}$ | $1.9^a$ | $3.6^c$ | $7.2^a$ | $4.0^b$ |
| 8-9 cm | NM | $12.4^b$ | $3.6^b$ | $4.0^a$ | $1.9^a$ | $6.2^b$ | $7.0^a$ | $4.2^b$ |
|  | Ma | $13.2^a$ | $4.8^a$ | $4.3^a$ | $2.0^a$ | $7.0^a$ | $7.2^a$ | $6.3^a$ |
|  | Mb | $13.1^a$ | $5.2^a$ | $4.2^a$ | $1.9^a$ | $7.4^a$ | $7.4^a$ | $6.5^a$ |

EXAMPLE 7

Enhancement of *Dendrobium candidum* Seedling Growth with Bio-Fertilizer After Deflasking from Tissue Culture The seedlings of *Dendrobium candidum* are planted in oat culture media after deflasking from tissue culture, and divided into 3 groups: no fertilizer group (NM control group); bio-fertilizer composition Ma (BCRC930076) added group from Example 3; and bio-fertilizer composition Mb (BCRC930077) added group from Example 3. The growth of seedlings of *Dendrobium candidum* in different groups is compared after 4 months. Each treatment contains 20 duplicates, and the data is analyzed with Duncan's multiple range test (DMRT) using p-value of 0.05.

As shown in Table 3, the addition of fertilizers (treatment groups) improved the growth of *Dendrobium candidum* in comparison with the control group, and the survival rates of treatment groups are 20% better than that of the control group.

EXAMPLE 8

Enhancement of *Phalaenopsis* Seeding Growth with Bio-Fertilizer During Tissue Culture The seedlings of *Phalaenopsis* are planted during tissue culture, and divided into 3 groups; no fertilizer group (control group); bio-fertilizer composition Ma (BCRC930076) added group from Example 3; and bio-fertilizer composition Mb (BCRC930077) added group from Example 3. The growth of seedlings of *Phalaenopsis* in different groups is compared after 4 months. Each treatment contains 5 duplicates, and the data is analyzed with Duncan's multiple range test (DMRT) using p-value of 0.05.

Figure 2:
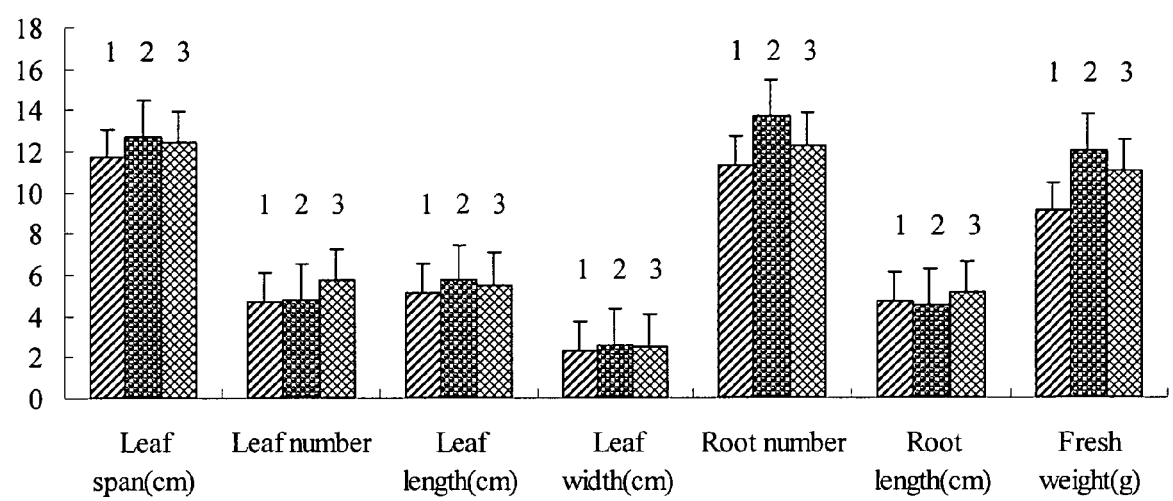
FIG. 2 shows the growth effects of bio-fertilizer compositions to *Phalaenopsis* seedling growth. 1. no fertilizer; 2. bio-fertilizer composition Ma is applied; 3. bio-fertilizer composition Mb is applied.

The effect of addition of fertilizers (treatment groups) in the growth of *Phalaenopsis* in comparison with the control group is shown in FIG. 2. The root numbers and fresh weights of treatment groups are significantly higher than those of the control group.

EXAMPLE 9

Enhancement of *Phalaenopsis* Seedling Growth with Bio-Fertilizer After Deflasking from Tissue Culture The seedlings of *Phalaenopsis* are planted after deflasking from tissue culture, and divided into 3 groups; no fertilizer group (NM control group); bio-fertilizer composition Ma (BCRC930076) added group from Example 3; and bio-fertilizer composition Mb (BCRC930077) added group from Example 3. After 4 months, the growth of seedlings of *Phalaenopsis* after deflasking in different groups is com-

TABLE 3

The effect of inoculaing bio-fertilizer composition for 4 months to seedlings of *Dendrobtian candidum* Wall. ex Linkl. after deflasking

| Treatment | Plant height (cm) | Length of pseudobulb (cm) | Width of pseudobulb (mm) | Number of leave | Root number | Auxiliary bud | Fresh weight (g) | Survival rate (%) |
|---|---|---|---|---|---|---|---|---|
| NM | $3.9^b$ | $2.6^a$ | $1.1^c$ | $8.3^c$ | $4.5^c$ | $3.7^{bc}$ | $0.3^b$ | 77 |
| Ma | $4.9^a$ | $3.2^a$ | $1.4^{ab}$ | $14^{ab}$ | $7.8^{ab}$ | $4.5^{abc}$ | $0.7^a$ | 97 |
| Mb | $5.0^a$ | $3.2^a$ | $1.3^{bc}$ | $15.6^a$ | $8.6^a$ | $5.7^a$ | $0.7^a$ | 95 | pared. Each treatment contained 5 duplicates, and the data is analyzed with Duncan's multiple range test (DMRT) using p-value of 0.05.

The bio-fertilizer composition Mb (treatment group) significantly increased the effective components of *Anoectochilus formosanus* to a large extent.

TABLE 5

Analysis of bioactive components superoxide dismutase (SOD), polysaccharids, polyphenols, phosphorus ions and vitamin C in the leave, stems and roots of *Anoectochilus formosanus*

| Treatment | Plant tissues | SOD (units/ml) | Polysaccharids (mg/ml) | Polyphenols (mg/ml) | Phosphorus ions (mg/l) | Vitamin C (mg/l) |
|---|---|---|---|---|---|---|
| NM | Leave | $21.1^b$ | $15.1^b$ | $5.2^{bc}$ | $336.0^b$ | $173.3^{ab}$ |
|  | Stem | $10.5^c$ | $1.2^d$ | $2.2^d$ | $297.5^b$ | $73.7^c$ |
|  | Root | $5.3^d$ | 6.8 | $4.5^c$ | $141.3^c$ | $80.0^c$ |
| Mb | Leave | $34.2^a$ | $22.8^a$ | $7.1^a$ | $452.4^a$ | $270.0^a$ |
|  | Stem | $12.4^c$ | $8.9^c$ | $3.9^{cd}$ | $331.2^b$ | $74.9^c$ |
|  | Root | $9.5^{cd}$ | $17.2^b$ | $6.2^b$ | $167.2^c$ | $135.9^b$ |

Figure 3:
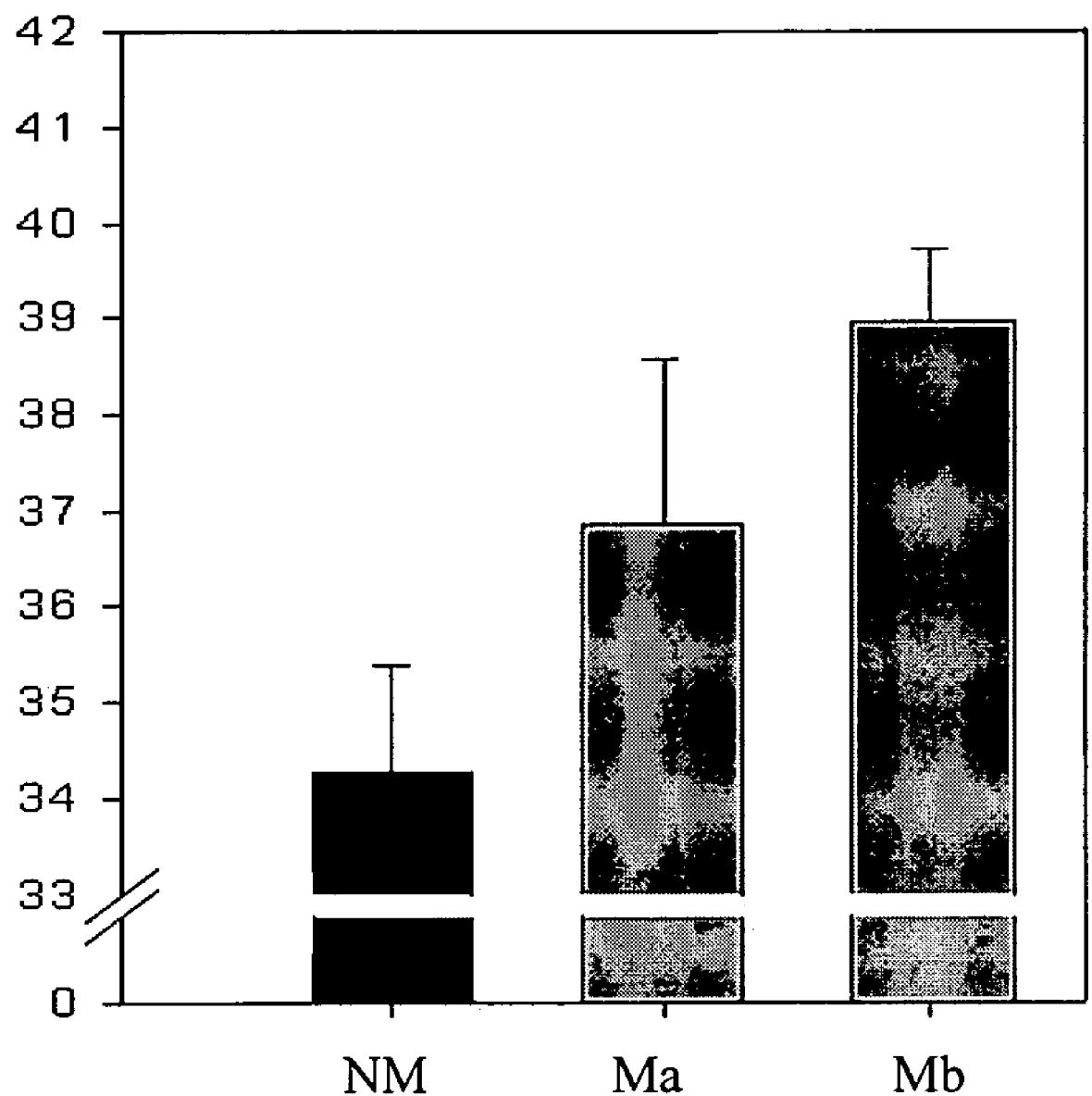
FIG. 3 shows the effects of bio-fertilizers on the amounts of chlorophyll in *Phalaenopsis*.

The effects of fertilizers (treatment groups) in the growth of *Phalaenopsis* in comparison with the control group are shown in FIG. 3. The contents of chlorophyll of treatment groups are significantly higher than those of the control group.

EXAMPLE 10

Enhancement of Flowering Rates with Bio-Fertilizer and Plant Growth Substance

*Phalaenopsis amabili* and *Doritaenopsis casablanca Joy* × *Phalaenopsis taida Pinlong* are treated with either bio-fertilizer composition Mb or plant growth regulators Gibberellic Acid ($GA_3$), or both. The flowering rates are observed after incubation.

As shown in Table 4, the addition of bio-fertilizer Mb and $GA_3$ (treatment groups) improved the growth of both *Phalaenopsis* to a large extent: 92% and 88% respectively, in comparison with 42% of the control group (NM), which is 50% better than that of the control group.

TABLE 4

The flowering rates of both *Phalaenopsis* after treatments of bio-fertilizer composition Mb and/or plant growth regulators gibberellic acid ($GA_3$) at room temperature

| Treatment | *Phalaenopsis amabilis* | *Doritaenopsis casablanca* Joy × *Phalaenopsis taida* Pinlong |
|---|---|---|
| NM | 42 | 42 |
| Mb | 42 | 45 |
| NM + $GA_3$ | 75 | 71 |
| Mb + $GA_3$ | 92 | 88 |

EXAMPLE 11

*Anoectochilus formosanus* is treated with either bio-fertilizer composition Mb (Mb) or nothing (NM). The changes on effective components are analyzed after incubation. The treatment contains 4 duplicates, and the data is analyzed with Duncan's multiple range test (DMRT) using p-value of 0.05.

Table 5 shows the comparison analysis of bioactive components with health benefits such as superoxide dismutase (SOD), polysaccharides, polyphenols, phosphorus ions and vitamin C with or without the addition of bio-fertilizer Mb.

What is claimed is:

1. A bio-fertilizer composition for promoting flowering rates of orchid plants, comprising:
    a symbiotic organism, which is selected from the group consisting of *Rhizoctonia* strains without pathogenicity containing *Rhizoctonia* sp. BCRC930076 and *Rhizoctonia* sp. BCRC930077, deposited with Food Industry Research and Development Industry, Taiwan;
    a growth substance selected from the group consisting of natural plant hormones and artificially synthesized plant growth regulators; and
    a medium, which is used to mix and evenly disperse the symbiotic organisms and the growth substance;
    wherein the natural plant hormones are selected from the group consisting of auxins, cytokines, abscisic acid, ethylene, brassinosteroids, jasmonate and salicylates.

2. The bio-fertilizer composition as claimed in claim 1, wherein the plant growth regulator is inositol.

3. The bio-fertilizer composition as claimed in claim 1, wherein the media are selected from the group consisting of peat moss, Sphagnum mosses, coconut fiber and rotting logs.

4. The bio-fertilizer composition as claimed claim 1, wherein the composition further comprises a nutrient solution.

5. The bio-fertilizer composition as claimed in claim 4, wherein the nutrient solution is selected from the group consisting of fruit and vegetable juices, GY nutrient solution, CM nutrient solution and food grade beverage.

6. The bio-fertilizer composition as claimed in claim 1, wherein the composition is a liquid form.

7. The bio-fertilizer composition as claimed in claim 1, wherein the composition is a solid form.

8. A method of enhancing beneficial components toward human health of medicinal orchids comprising mixing into peat moss, Sphagnum mosses, coconut fiber, fern chips or rotting logs in which medicinal orchids are growing or are to be grown a growth enhancing quantity of the bio-fertilizer composition of claim 1.

9. The method as claimed in claim 8, wherein the beneficial components are selected from the group consisting of superoxide dismutase (SOD), polysaccharides, polyphenols, phosphorus ions, total phenolic compounds, and vitamin C.

10. The method as claimed in claim 8, wherein the medicinal orchid comprises *Anoectochilus formosanus*.

* * * * *